United States Patent [19]

Kraus et al.

[11] Patent Number: 5,183,884

[45] Date of Patent: Feb. 2, 1993

[54] DNA SEGMENT ENCODING A GENE FOR A RECEPTOR RELATED TO THE EPIDERMAL GROWTH FACTOR RECEPTOR

[75] Inventors: Matthias H. Kraus, Bethesda, Md.; Stuart A. Aaronson, Vienna, Va.

[73] Assignee: United States of America, Washington, D.C.

[21] Appl. No.: 444,406

[22] Filed: Dec. 1, 1989

[51] Int. Cl.$^5$ .................. C07H 15/12; C12N 1/20; C12N 15/00

[52] U.S. Cl. .................. 536/23.5; 536/23.1; 435/252.3; 435/320.1

[58] Field of Search ............. 536/26, 27, 28; 935/71, 935/22; 435/250.3, 252.33, 320.1

[56] References Cited

PUBLICATIONS

Anti-erbB MaBs : hybridomas HB 9097 & HB 9098, ATCC Catalog 7th edn., 1992, p. 415.

Coussens et al., Science 230:1132–1139 (Dec. 6, 1985).

Improved Tools for Biological Sequence Comparison–William R. Pearson and David J. Lipman.

Signal Transduction Through the EGF Receptor Transfected in Il-3-Dependent Hematopoietic Cells–Jacalyn H. Pierce, Marco Ruggiero, Timothy P. Fleming, Pier Paolo Di Fiore, Joel S. Greenberger, Lyubra Varticovski, Joseph Schlessinger Giovannia Rovera, and Stuart A. Aaronson.

Overexpression of the EGF Receptor-Related Proto-Oncogene erbB-2 in Human Mammary Tumor Cell Lines by Different Colecular Mechanisms–Matthias H. Kraus, Nicholas C. Popescu, Suzanne C. Amsbaugh and C. Richer King.

Amplification of a Novel v-erB-related gene in a human mammary carcinoma. King, Kraus and Aaronson. Science, vol. 229 Sep. 6, 1985.

Similarity of protein encoded by the human c-erb-B-2 gene to epidermal growth factor receptor. Yamamoto, Ikawa, Akiyama, Semba, Nomura, Miyajima, Saito and Toyoshima. Nature vol. 319 Jan. 16, 1986.

erb-2 Is a Potent Oncogene When overexpressed in NIH/3T3 Cells. Di Fiore, Pierce, Kraus, Segatto, King and Aaronson. Science, vol. 237 Jul. 10, 1987.

Isolation and characterization of ERBB3, a third member of the ERBB/epidermal growth factor receptor family: Evidence for overexpression in a subset of human mammary tumors. M. Kraus, W. Issing, T. Miki, N. Popescu and S. Aaronson; Proc. Natl. Acad. Sci. USA vol. 86, pp. 9193–9197, Dec. 1989 Biochemistry.

A v-erbB-related protooncogene, c-erbB-2, is distinct from the c-erbB-1/epidermal growth factor-receptor gene is amplified in a human salivary gland adenocarcinoma. K. Semba, N. Kamata, K. Toyoshima and T. Yamamoto Proc. Natl. Acad. Sci., USA vol. 82, pp. 6497–6501, Oct. 1985 Biochemistry.

Primary Examiner—Margaret Moskowitz
Assistant Examiner—Stephanie W. Zitomer
Attorney, Agent, or Firm—Cushman, Darby & Cushman

[57] ABSTRACT

A DNA fragment distinct from the epidermal growth factor receptor (EGF-R) and erbB-2 genes was detected by reduced stringency hybridization of v-erbB to normal genomic human DNA. Characterization of the cloned DNA fragment mapped the region of v-erbB homology to three exons with closest homology of 64% and 67% to a contiguous region within the tyrosine kinase domains of the EGF-R and erbB-2 proteins, respectively. cDNA cloning revealed a predicted 148 kd transmembrane polypeptide with structural features identifying it as a member of the erbB family, prompting designation of the new gene as erbB-3. It was mapped to human chromosome 12q11-13 and was shown to be expressed as a 6.2 kb transcript in a variety of normal tissues of epithelial origin. Markedly elevated erbB-3 mRNA levels were demonstrated in certain human mammary tumor cell lines. These findings indicate that increased erbB-3 expression, as in the case of EGF-R and erbB-2, plays a role in some human malignancies.

8 Claims, 21 Drawing Sheets

FIG. 2
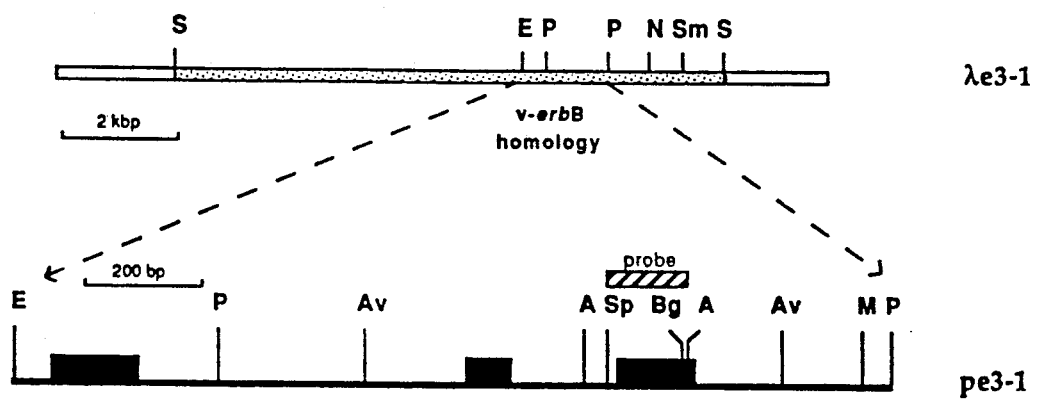
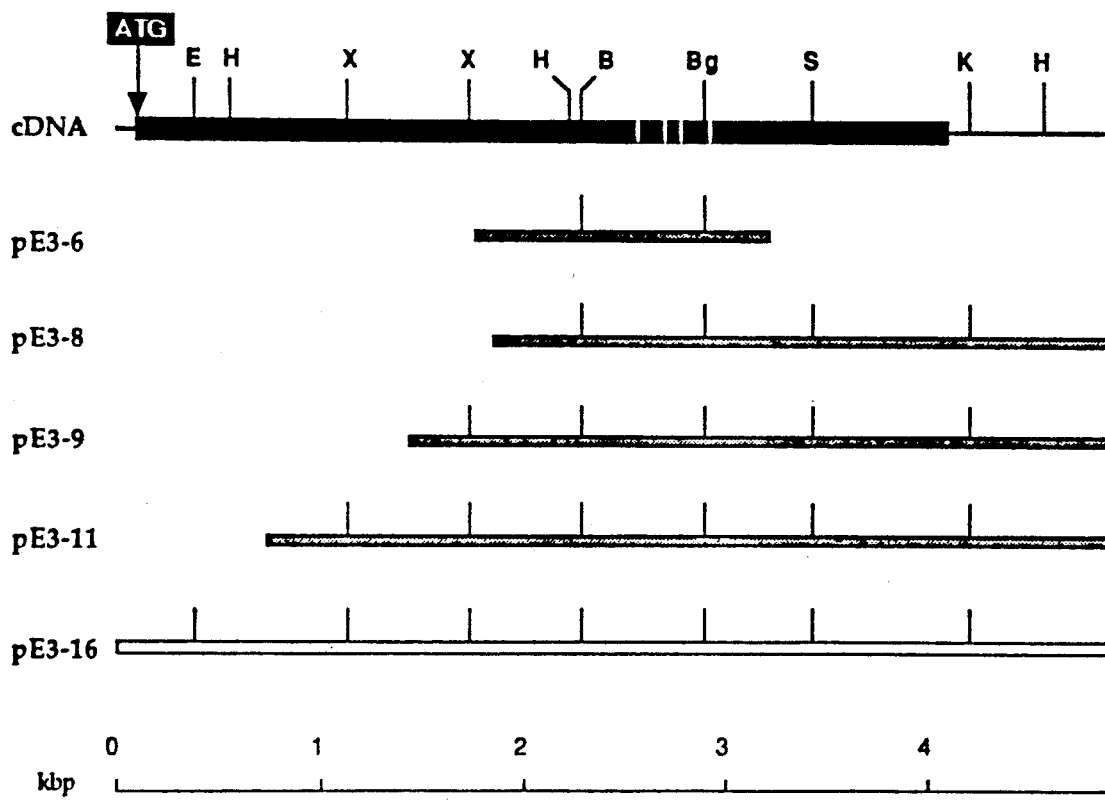

FIG. 3

GAATTCCAGATCTCAGTGACTGATTCCCCAACCTTAAGAATACTTTCTTCCCCTATACCTACAG

| Gly | Met | Tyr | Tyr | Leu | Glu | Glu | His | Gly | Met | Val | His | Arg | Asn | Leu | Ala | Ala |
|---|---|---|---|---|---|---|---|---|---|---|---|---|---|---|---|---|
| GGA | ATG | TAC | TAC | CTT | GAG | GAA | CAT | GGT | ATG | GTG | CAT | AGA | AAC | CTG | GCT | GCC |

| Arg | Asn | Val | Leu | Leu | Lys | Ser | Pro | Ser | Gln | Val | Ala | Asp | Phe | Gly |
|---|---|---|---|---|---|---|---|---|---|---|---|---|---|---|
| CGA | AAC | GTG | CTA | CTC | AAG | TCA | CCC | AGT | CAG | GTT | GCA | GAT | TTT | GGT |

| Val | Ala | Asp | Leu | Leu | Pro | Pro | Asp | Asp | Lys | Gln | Leu | Leu | Tyr | Ser | Glu | Ala |
|---|---|---|---|---|---|---|---|---|---|---|---|---|---|---|---|---|
| GTG | GCT | GAC | CTG | CTG | CCT | CCT | GAT | GAT | AAG | CAG | CTG | CTA | TAC | AGT | GAG | GCC |

| Lys |
|---|
| AAG | GTGAGGAGACACAAAGGGTAAGGAGGGTGGAGTGAAGCATGGGGATAGGGAGCAGCCA

GTGGTCTCTTCCAGAGGCAAGCCAGATGCTTCATGGTAAGTTCAAGGAGAGAAGGCTGCAGATGCCAG
ATATTTAGTTCAGAGGCAACAACAAAGAAATGATCAAGAACTTGGGACTGGCCGGGCGCGGTGG
CTCACGCCTGTAATCCCAACACTTCGGGAGGCCAAGGCGGGTGGATCACAAGGTCAGGAGATCAAGA
CCATCCTGGCTAACACGGTGAAACCCCGTCTCTACTAAAAATATACAAAAAAATTAGCCAGGC
GTGGCGGCATGCATGCTTGTACTCGGGAGGCTGAGGCAGGAGAATGGCGTGAACCCAGG
AGGCGGAGCTTGCAGTGGCCGAGATCGCGCCACTCCAGTCTGGGCGACAGAGCGAGACTCC
GTCTCAAAAAAAAAAAAAAAAGAATTTGGGACTTGGAAATCCTAAGAAATCCTAAGAAAATTTGTGGAAATAAACTT

FIG. 3 CONT.'

```
                              Thr Pro Ile Lys Trp Met Ala Leu Glu Ser
GTGATACCCTCTATCTTTAATCCGCAG ACT CCA ATT AAG TGG ATG GCC CTT GAG AGT

Ile His Phe Gly Lys Tyr Thr His Gln Ser Asp Val Trp Ser Tyr G
ATC CAC TTT GGG AAA TAC ACA CAC CAG AGT GAT GTC TGG AGC TAT G GTCAG

TGCATCTGGATGCCCTCTCTACCATCACTGGCCCCAGTTTCAAATTTACCTTTTGAGAGCCCCCTCT
TAGAATCTCTAAGCACTTCAGATTTTGTGTTAGATCAGGTTCTGCCTTCCCTTCACTTCATGCCCA ly Val Thr Val Trp Glu
TGTCTACTATTTGCCAGTGACTAGTCCATGTCTCCTGCAACAG GT GTG ACA GTT TGG GAG

Leu Met Thr Phe Gly Ala Glu Pro Tyr Ala Gly Leu Arg Leu Ala Glu Val
TTG ATG ACC TTC GGG GCA GAG CCC TAT GCA GGG CTA CGA TTG GCT GAA GTA

Pro Asp Leu Leu Glu Lys Gly Glu Arg Leu Ala Gln Pro Gln Ile Cys Thr
CCA GAC CTG CTA GAG AAG GGG GAG CGG TTG GCA CAG CCC CAG ATC TGC ACA

Ile Asp Val Tyr Met Val Met Val Lys
ATT GAT GTC TAC ATG GTG ATG GTC AAG T GTGAGTTACCTGCTGAGCCCAACCATTT

CTCTTTTTTCTTTTTTTTCTTTTTTTTTTGAGACAGAGTCTCACAATTGTCACCCAGGC
TGGAGTGCAATGGTGCAATCAATCTTGGCTCACTACAACCTCCGCCTCTCGGGTTCAAGAGATTCTC
CTGCTTCAGCTCCGAGTAGCTGGGATTACAGGCCCGCCACCACCTGGATAACTGTTACACTTTTAG
TAGAGATGGGGTTTCACCATGTTGGCCAGGCTGGTCTCAAACTCCTGACCTCAGGTGATCCGCCTGC
CTCAGCTTCCCAAAGTGCTGGGATTACAGAGTGTGAGCCATCATGCTCGCCTGACTGCAG
```

FIG. 4A

```
1    ACCAATTCGCCAGCGGTTCAGGTGGCTCTTGCCTCGATGTCCTAGCCTAGGGCCCCCGGGCCGGACTTG
                                              MetArgAlaAsnAspAlaLeu
     GCTGGGCTCCCTCACCCTCTGCGAGTCATGAGGGCGAACGACGCTCTG
        GlnValLeuGlyLeuLeuPheSerLeuAlaArgGlySerGluValGlyAsnSerGlnAlaValCysProGly
                                                           10                              20                                                  30
121  CAGGTGCTGGGCTTGCTTTTCAGCCTGGCCCGGGGCTCCGAGGTGGGCAACTCTCAGGCAGTGTGTCCTGGG
        ThrLeuAsnGlyLeuSerValThrGlyLeuAspAlaGluAsnGlnTyrGln
     ACTCTGAATGGCCTGAGTGTGACCGGCGATGCTGAGAACCAATACCAG
                         50                                                60                                                 70
        ThrLeuTyrLysLeuTyrGluArgCysGluValValValLeuThrGlyAsnLeuMetGlyAsnLeuGluIleValLeuThrGlyHisAsn
241  ACACTGTACAAGCTCTACGAGAGGTGTGAGGTGGTGGTGCTGACTGGGAACCTTATGGGAAACCTTGAGATTGTGCTCACGGGACACAAT
        AlaAspLeuSerPheLeuGlnTrpIleArgGluValThrGlyTyrVal
                         80
     GCCGACCTCTCCTTCCTGCAGTGGATTCGAGAAGTGACACAGGCTATGTC
        LeuValAlaMetAsnGluPheSerThrLeuProLeuProAsnLeuArgValValAlaArgGlyThrGlnValTyr
                         90                                                 100                                                110
361  CTCGTGGCCATGAATGAATTCTCTACTCTGCCCAACCTCCGCGTTGTGGCGAGGGGACCCAGGTCTAC
        AspGlyLysPheAlaIlePheValMetLeuAsnTyrAsnThrAsnSer
                         120
     GATGGGAAGTTTGCCATCTTCGTCATGTTGAACTATAACACCAACTCC
```

FIG. 4B

```
            130                           140                            150
    SerHisAlaLeuArgGlnLeuArgLeuThrGlnLeuThrGluIleLeuLeuSerGlyGlyValTyrIleGluLys
481 AGCCACGCTCTGCGCCAGCTCCGCTTGACTCAGCTCACCGAGATTCTGTCAGGGGGTGTTTATATTGAGAAG 160                           170
    AsnAspLysLeuCysHisMetAspThrIleAspTrpArgAspIleVal
    AACGATAAGCTTTGTCACATGGACACAATTGACTGGAGGGACATCGTG 170                           180                            190
    ArgAspArgAspAlaGluIleValValValLysAspAsnGlyArgSerCysProProCysHisGluValCysLys
601 AGGGACCGAGATGCTGAGATAGTGGTGGTGAAGGACAATGGCAGAAGCTGTCCCCCTGTCATGAGGTTTGCAAG 200                          210
    GlyArgCysTrpGlyProGlySerGluAspCysGlnThrLeuThrLys
    GGGCGATGCTGGGGGTCCTGGGATCAGAAGACATTGACCAAG 210                           220                            230
    ThrIleCysAlaProGlnCysAsnGlyHisCysPheGlyProAsnProAsnGlnCysCysHisAspGluCys
721 ACCATCTGTGCTCCTCAGTGTAATGGTCACTGCTTTGGGCCCAACCCCAACCAGTGCTGCCATGATGAGTGT

240
    AlaGlyGlyCysSerGlyProGlnAspThrAspCysPheAlaCysArg
    GCCGGGGGCTGCTCAGGCCCTCAGGACACAGACTGCTTTGCCTGCCGG
```

FIG. 4C

```
                250                      260                      270
     HisPheAsnAspSerGlyAlaCysValProArgCysProGlnProLeuValTyrAsnLysLeuThrPheGln
841  CACTTCAATGACAGTGGAGCCTGTGTACCTCGCTGTCCACAGCCTCTTGTCTACAACAAGCTAACTTTCCAG

LeuProAsnProHisThrLysTyrGlnTyrGlyValGlyCysVal
     CTGGAACCCCATCCCCACACCAAGTATCAGTATGGAGGAGTTTGTGTA 290                      300                      310
     AlaSerCysProHisAsnPheValValAspGlnThrSerCysValArgAlaCysProProAspLysMetGlu
961  GCCAGCTGTCCCCATAACTTTGTGGTGGATCAAACATCCTGTGTCAGGGCCTGTCCTCCTGACAAGATGGAA

320
     ValAspLysAsnGlyLeuLeuLysMetCysGluProCysGlyGlyLeuCys
     GTAGATAAAAATGGGCTCAAGATGTGTGAGCCTTGTGGGGGACTATGT 330                      340                      350
     ProLysAlaCysGluGlyThrGlySerGlyArgPheGlnThrValAspSerSerAsnIleAspGly
1081 CCCAAGGCCTGTGAGGGAACAGGCTCTGGGAGGCGCTTCCAGACTGTGGACTCGAGCAACATTGATGGA

360
     PheValAsnCysThrLysIleLeuGlyAsnLeuAspPheLeuIleThrGly
     TTTGTGAACTGCACCAAGATCCTGGGCAACCTGGACTTTCTGATCACCGGC
```

FIG. 4D

```
                                                      380                                                390
     LeuAsnGlyAspProTrpHisLysIleProAlaLeuAspProGluLysLeuLeuAsnValPheArgThrValArg
1201 CTCAATGGAGACCCCTGGCACAAGATCCCTGCCCTGGACCCCAGAGAAGCTCAATGTCTTCCGGACAGTACGG

GluIleThrGlyTyrLeuAsnIleGlnSerTrpProProHisMetHis
     GAGATCACAGGTTACCTGAACATCCAGTCCTGGCCGCCCCACATGCAC 420                                                430
     AsnPheSerValPheSerAsnLeuThrThrIleGlyGlyArgSerLeuTyrAsnArgArgGlyPheSerLeuLeu
1321 AACTTCAGTGTTTTTTCCAATTTGACAACCATTGGAGGCAGAAGCCTCTACAACCGGGGCTTCTCATTGTTG

IleMetLysAsnLeuThrSerLeuGlyPheArgSerLeuLys
     ATCATGAAGAACTTGAATGTCACATCTCTGGGCTTCCGATCCCTGAAG 460                                                470
     GluIleSerAlaGlyArgIleTyrIleSerAlaAsnArgGlnLeuCysTyrHisHisSerLeuAsnTrpThr
1441 GAAATTAGTGCTGGGCGTATCTATATAAGTGCCAATAGGCAGCTCTGCTACCACCACTCTTTGAACTGGACC

LysValLeuArgGlyProThrGluArgLeuAspIleLysHisAsn
     AAGGTGCTTCGGGGGCCTACGGAAGAGAGGCGACTAGACATCAAGCATAAT
```

FIG. 4E

```
                                    500                                  510
     ArgProArgArgAspCysValAlaAlaGluGlyLysValAspProLeuCysSerSerGlyGlyCysTrpGly
1561 CGGCCCGGCGAGAGACTGGTGGCAGAGGGCAAAGTGTGACCCACTGTGCTCCTCTGGGGGATGCTGGGGC

ProGlyProGlyGlnCysLeuSerCysArgAsnTyrSerArgGlyGly
                    520
     CCAGGCCCTGGTGCAGTGCTTGTCCTGTCGAAATTATAGCCGAGGAGGT

540
     ValCysValThrHisCysAsnPheLeuAsnGlyGluProArgGluPheAlaHisGluAlaGluCysPheSer
1681 GTCTGTGTGACCCACTGCAACTTTCTGAATGGGGAGCCTCGAGAATTTGCCCATGAGGCCGAATGCTTCTCC

CysHisProGluCysGlnProMetGluGlyThrAlaThrCysAsnGly
                 560
     TGCCACCCGGAATGCCAACCCATGGAGGGCACTGCCACATGCAATGGC 580                                  590
     SerGlySerAspThrCysAlaGlnCysAlaHisPheArgAspGlyProHisCysValSerSerCysProHis
1801 TCGGGCTCTGATACTTGTGCTCAATGTGCCCATTTTCGAGATGGGCCCCACTGTGTGAGCAGCTGCCCCCAT

GlyValLeuGlyAlaAlaLysGlyProIleTyrLysTyrProAspValGln
                     600
     GGAGTCCTAGGTGCCAAGGGCCCAATCTACAAGTACCCAGATGTTCAG
```

FIG. 4F

```
                    610              Cys         Cys   620                       Cys    630
            AsnGluCysArgProCysHisGluAsnCysThrGlnGlyCysLysGlyProGluLeuGlnAspCysLeuGly
      1921  AATGAATGTCGGCCCTGCCATGAGAACTGCACCCAGGGTGTAAAGGACCAGAGCTTCAAGACTGTTTAGGA

640
            GlnThrLeuValLeuIleGlyLysThrHisLeuThrMetAlaLeuThr
            CAAACACTGGTCCTGATCGGCAAAACCCATCTGACAATGGCTTTGACA 650                          660
            ValIleAlaGlyLeuValValIlePheMetMetLeuGlyGlyThrPheLeuTyrTrpArgGlyArgArgIle
      2041  GTGATAGCAGGATTGGTAGTCATTTTCATGATGCTGGGCGGCACTTTTCTCTACTGGCGTGGGCGCCGGATT

680
            GlnAsnLysArgAlaMetArgArgTyrLeuGluArgGlyGluSerIle
            CAGAATAAAAGGGCTATGAGGCGATACTTGGAACGGGGTGAGAGCATA 690                          700                       710
            GluProLeuAspProSerGluLysAlaAsnLysValLeuAlaArgIlePheLysGluThrLeuArgLys
      2161  GAGCCTCTGGACCCCAGTGAGAAGGCTAACAAAGTCTTGGCCAGAATCTTCAAAGAGACAGAGCTAAGGAAG

*     *     *     720  *
            LeuLysValLeuGlySerGlyValPheGlyThrValHisLysGlyVal
            CTTAAAGTGCTTGGCTCGGGTGTCTTTGGAACTGTGCACAAAGGAGTG
```

FIG. 4G

```
                730                    740  *              750
      TrpIleProGluglyGluSerIleLysIleProValCysIleLysValIleGluAspLysSerGlyArgGln
2281  TGGATCCCCTGAGGGTGAATCAATCAAGATTCCAGTCTGCATTAAAGTCATTGAGGACAAGAGTGGACGGCAG SerPheGlnAlaValThrAspHisMetLeuAlaIleGlySerLeuAsp
      AGTTTTCAAGCTGTGACAGATCATATGCTGGCCATTGGCCAGCCTGGAC 770                    780                790
      HisAlaHisIleValArgLeuLeuGlyLeuLysLeuCysProGlySerSerLeuGlnLeuValThrGlnTyrLeuPro
2401  CATGCCCACATTGTAAGGCTGCTGGGACTATGCCCAGGGTCATCTCTGCAGCTTGTCACTCAATATTGCCT LeuGlySerLeuLeuAspHisValArgGlnHisArgGlyAlaLeuGly
      CTGGGTTCTCTGCTGGATCATGTGAGACAACACCGGGGGGCACTGGGG 810                    820                830
      ProGlnLeuLeuLeuAsnTrpGlyValGlnIleAlaLysGlyMetTyrTyrLeuGluGluHisGlyMetVal
2521  CCACAGCTGCTGCTCAACTGGGGAGTACAAATTGCCAAGGGATACTACCTTGAGGAACATGGTATGGTG 840
      HisArgAsnLeuAlaAlaArgAsnValLeuLeuLysSerProSerGln
      CATAGAAACCTGGCTGCCCGAAACGTGCTACTCAAGTCACCCAGTCAG
```

FIG. 4H

```
                   850                                              870
       ValGlnValAlaAspPheGlyValAlaAspLysProProAspAspLysGlnLeuLeuTyrSerGluAla
2641   GTTCAGGTGGCAGATTTGGTGTGGCTGACCTGCCTGCTCCTGATGATAAGCAGCTGCTATACAGTGAGGCC

880
       LysThrProIleLysTrpMetAlaLeuGluSerIleHisPheGlyLys
       AAGACTCCAATTAAGTGGATGGCCCTTGAGAGTATCCACTTTGGGAAA 890                                              910
       TyrThrHisGlnSerAspValTrpSerTyrTyrGlyValThrValTrpGluLeuMetThrPheGlyAlaGluPro
2761   TACACACACCAGAGTGATGTCTGGAGCTATTATGGAGTTACAGTTTGGGAGTTGATGACCTTCGGGGCAGAGCCC

900
       TyrAlaGlyLeuArgLeuAlaGlyValProAspLeuValLeuLysGly
       TATGCAGGGCTACGATTGGCTGAAGTACCAGAGACCTGCTAGAGAAGGGG 930                                              950
       GluArgLeuAlaGlnProGlnIleCysThrIleAspValTyrMetValLysCysTrpMetIleAsp
2881   GAGCGGTTGGCACAGCCCCAGATCTGCACAATTGATGTCTACATGGTCAAGTGTTGGATGATTGAT

960
       GluAsnIleArgProThrPheLysGluLeuAlaAsnGluPheThrArg
       GAGAACATTCGCCCAACCTTTAAAGAACTAGCCAATGAGTTCACCAGG
```

FIG. 4I

```
                                970                                           980                                               990
         MetAlaArgAspProProArgTyrLeuValIleLysArgGluSerGlyProGlyIleAlaProGlyProGlu
3001     ATGGCCCGAGACCCACCACGGTATCTGGTCATAAAGAGAGAGTGGGCCTGGAATAGCCCCTGGGCCAGAG

1000
         ProHisGlyLeuThrAsnLysLysLeuGluGluValGluLeuGluPro
         CCCCATGGTCTGACAAACAAGAAGCTAGAGGAAGTAGAGCTGGAGCCA 1010                                          1020                                              1030
         GluLeuAspLeuAspLeuGluAlaGluLeuAspAsnLeuAlaThrThrThrLeuGlySerAlaLeu
3121     GAACTAGACCTAGACCTAGAGGCAGAGCTGGACAACCTGGCAACCACCACACTGGGCTCCGCCCTC

1040
         SerLeuProValGlyThrLeuAsnArgProArgGlySerGlnSerLeu
         AGCCTACCAGTTGGAACACTTAATCGGCCACGTGGGAGCCAGAGCCTT 1050                                          1060                                              1070
         LeuSerProSerSerGlyTyrMetProMetAsnGlnGlyAsnLeuGlyLeuGluSerCysGlnGluSerAlaVal
3241     TTAAGTCCATCATCTGGATACATGCCCATGAACCAGGGTAATCTTGGGGAGTCTTGCCAGGAGTCTGCAGTT

1080
         SerGlySerSerGluArgCysProArgProValSerLeuHisProMet
         TCTGGGAGCAGTGAACGGTGCCCCCGTCCAGTCTCTCTACACCCAATG
```

FIG. 4J

```
            1090                                            1100                                          1110
            ProArgGlyGlyCysLeuAlaSerGluSerSerGluGlyHisValThrGlySerGluAlaGluLeuGlnGluLys
3361        CCACGGGGATGGCTGTCTGGCATCAGAGTCATCAGAGGGCATGTAACAGGCTCTGAGGCTCCAGGAGAAA

1120
            ValSerMetCysArgSerArgSerArgSerArgProArgProArg
            GTGTCAATGTGTAGAAGCCGGAGCAGGAGCCGGAGCCCACGGCCACGC 1130                                            1140                                          1150
            GlyAspSerAlaTyrHisSerGlnArgHisSerLeuLeuThrProValThrProLeuSerProProGlyLeu
3481        GGAGATAGCGCCTACCATTCCCAGCGCCACAGTCTGCTGACTCCTGTTACCCCACTCTCCCCACCCGGGTTA

1160
            GluGluGluAspValAsnGlyTyrValMetProAspThrHisLeuLys
            GAGGAAGAGGATGTCAACGGTTATGTCATGCCAGATACACACCTCAAA 1170                                            1180                                          1190
            GlyThrProSerSerArgGluGlyThrLeuSerSerValGlyLeuSerSerValLeuGlyThrGluGluGlu
3601        GGTACTCCCTCCTCCCGGGAAGGCACCCTTTCTTCAGTGGTCTTAGTTCTGTCCTGGTACTGAAGAAGAA

↓1200
            AspGluAspGluGluTyrGluTyrMetAsnArgArgArgArgHisSer
            GATGAAGATGAGGAGTATGAATACATGAACCGGAGGAGAAGGCACAGT
```

FIG. 4K

```
              1210                1220                          1230
       ProProHisProProArgProSerLeuGluLeuGlyLeuLeuGlyTyrGluTyrMetAspValGlySerAspLeu
3721   CCACCCTCATCCCCCTAGGCCAAGTTCCCTTGAGGAGCTGGGTTATGAGTACATGGATGTGGGGTCAGACCTC

1240
       SerAlaSerLeuGlySerThrGlnSerCysProLeuHisProValPro
       AGTGCCTCTCTGGGCAGCACACAGAGTTGCCCACTCCACCCTGTACCC 1250              1260 →                          1270
       IleMetProThrAlaGlyThrThrProAspGluAspTyrGluTyrMetAsnArgGlnArgAspGlyGlyGly
3841   ATCATGCCCACTGCAGGCACAACTCCAGAAGACTATGAATATATGAATCGGCAACGAGATGGAGGTGGT

1280
       ProGlyGlyAspTyrAlaAlaMetGlyAlaCysProAlaSerGluGln
       CCTGGGGGTGATTATGCAGCAATGGGGGCCTGCCCCAGCATCTGAGCAA 1290                    1300                      1310
       GlyTyrGluGluMetArgAlaPheGlnGlyProGlyHisGlnAlaProHisValHisTyrAlaArgLeuLys
       GGGTATGAAGAGATGAGAGCTTTTCAGGGCCCTGGACATCAGGCCCCCATGTCCATTATGCCCGCCTAAAA

1320
       ThrLeuArgSerLeuGluAlaThrAspSerAlaPheAspAsnProAsp
3961   ACTCTACGTAGCTTAGAGGCTACAGAGACTCTGCCTTTGATAACCCTGAT
```

FIG. 4L

```
            1330
TyrTrpHisSerArgLeuPheProLysAlaAsnAlaGlnArgThrEnd
                                1340
4081 TACTGGCATAGCAGGCTTTTCCCCAAGGCTAATGCAGCCCAGAGAACGTAACTCCTGCTCCCGTGTGGCACTCAG
     GGAGCATTTAATGGCAGCTAGTGCCTTTAGAGGGTACCGTCTTCCCT
4201 ATTCCCTCTCTCTCCCAGTCCCAGCCCCTTTCCCCAGTCCCAGACAATTCCATTCAATCTTTGGAGGCT
     TTTAAACATTTGACACAAATTCTTATGGTATGTAGCCAGCTGTGCAC
4321 TTTCTCTCTTCTTCCCAACCCCAGGAAAGGTTTTCCTTATTTTGTGCTTTCCCAGTCCCATTCCCTCAGC
     TTCTTCACAGGCACTCCTGGAGATATGAAGGATTACTCTCCATATCCCTT
4441 CCTCTCAGGCTCTCTGACTACTGGAACTAGGGCTCTTATGTGTGCCTTTGTTCCCATCAGACTGTCAAGA
     AGAGGAAAGGGAGGAAACCTAGCAGAGGAAAGTGTAATTTGGTTTATGA
4561 CTCTTAACCCCCCTAGAAAGACAGAAGCTTAAAATCTGTGAAGAAAGAGGTTAGGAGTAGATATTGATTAC
     TATCATATAATTCAGCACTTAACTATGAGCCAGGCATCATAAACTTCAC
4681 CTACATTATCTCACTTAGTCCTTTATCATCCTTAAAACAATTCTGTGACATACATATTATCTCATTTTAC
     ACAAAGGGAAGTCGGGCATGGTGGCTCATGCCTGTAATCTCCAGCACTTTG
4801 GGAGGCTGAGGCAGAAGGATTACCTGAGGCAAGGAGTTTGAGACCAGCTTAGCCAACATAGTAAGACCCC
     CATCTCTTAAAAAAAAAAAAAAAAAAAAAAAAA
```

FIG. 5

```
   1  MRANDALQVL  GLLFSLARGS  EVGNSQAVCP  GTLNGLSVTG  DAENQYQTLY  KLYERCEVVM
  61  GNLEIVLTGH  NADLSFLQWI  REVTGYVLVA  MNEFSTLPLP  NLRVVRGTQV  YDGKFAIFVM
 121  LNYNTNSSHA  LRQLRLTQLT  EILSGGVYIE  KNDKLCHMDT  IDWRDIVRDR  DAEIVVKDNG
 181  RSCPPCHEVC  KGRCWGPGSE  DCQTLTKTIC  APQCNGHCFG  PNPNQCCHDE  CAGGCSGPQD
 241  TDCFACRHFN  DSGACVPRCP  QPLVYNKLTF  QLEPNPHTKY  QYGGVCVASC  PHNFVVDQTS
 301  CVRACPPDKM  EVDKNGLKMC  EPCGGLCPKA  CEGTGSGSRF  QTVDSSNIDG  FVNCTKILGN
 361  LDFLITGLNG  DPWHKIPALD  PEKLNVFRTV  REITGYLNIQ  SWPPHMHNFS  VFSNLTTIGG
 421  RSLYNRGFSL  LIMKNLNVTS  LGFRSLKEIS  AGRIYISANR  QLCYHHSLNW  TKVLRGPTEE
 481  RLDIKHNRPR  RDCVAEGKVC  DPLCSSGGCW  GPGPGQCLSC  RNYSRGGVCV  THCNFLNGEP
 541  REFAHEAECF  SCHPECQPME  GTATCNGSGS  DTCAQCAHFR  DGPHCVSSCP  HGVLGAKGPI
 601  YKYPDVQNEC  RPCHENCTQG  CKGPELQDCL  GQTLVLIGKT  HLTMALTVIA  GLVVIFMMLG
 661  GTFLYWRGRR  IQNKRAMRRY  LERGESIEPL  DPSEKANKVL  ARIFKETELR  KLKVLGSGVF
 721  GTVHKGVWIP  EGESIKIPVC  IKVIEDKSGR  QSFQAVTDHM  LAIGSLDHAH  IVRLLGLCPG
 781  SSIQLVTQYL  PLGSLLDHVR  QHRGALGPQL  LLNWGVQIAK  GMYYLEEHGM  VHRNLAARNV
 841  LLKSPSQVQV  ADFGVADLLP  PDDKQLLYSE  AKTPIKWMAL  ESIHFGKYTH  QSDVWSYGVT
 901  VWELMTFGAE  PYAGIRLAEV  PDLLEKGERL  AQPQICTIDV  YMVMVKCWMI  DENIRPTFKE
 961  LANEFTRMAR  DPPRYLIVKR  ESGPGIAPGP  EPHGLTNKKL  EEVELEPELD  LDLDLEAEED
1021  NLATTLGSA   LSLPVGTLNR  PRGSQSLLSP  SSGYMPMNQG  NLGESCQESA  VSGSSERCPR
1081  PVSLHPMPRG  CLASESSEGH  VTGSEAELQE  KVSMCRSRSR  SRSPRPRGDS  AYHSQRHSLL
1141  TPVTPLSPPG  LEEEDVNGYV  MPDTHLKGTP  SSREGTLSSV  GLSSVLGTEE  EDEDEEYEYM
1201  NRRRHSPPH   PPRPSSLEEL  GYEYMDVGSD  LSASLGSTQS  CPLHPVPIMP  TAGTTPDEDY
1261  EYMNRQRDGG  GPGGDYAAMG  ACPASEQGYE  EMRAFQGPGH  QAPHVHYARL  KTLRSLEATD
1321  SAFDNPDYWH  SRLFPKANAQ  RT
```

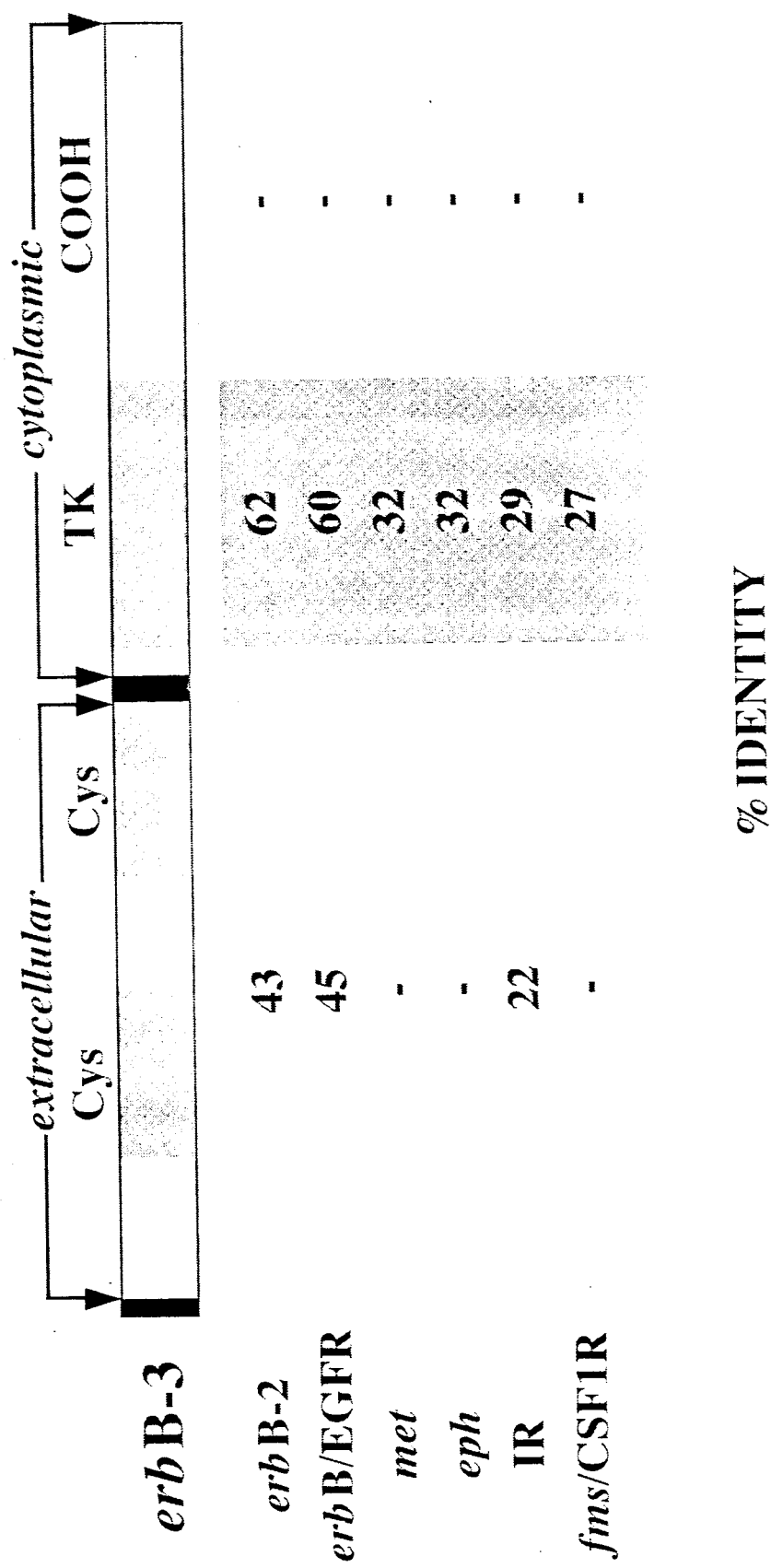
FIG. 5 CONT.'

```
          1  2    kD
                 —200
erbB-3 →  ▬

DNA SEGMENT ENCODING A GENE FOR A RECEPTOR RELATED TO THE EPIDERMAL GROWTH FACTOR RECEPTOR

FIELD OF THE INVENTION

The present invention relates to genes which encode novel proteins related to a family of receptor proteins typified by two related membrane spanning tyrosine kinases: the Epidermal Growth Factor receptor (EGF-R), which is encoded by the erbB gene, the normal human counterpart of an oncogene (v-erbB) that was first recognized in the proviral DNA of avian erythroblastosis virus; and the receptor encoded by the related gene erbB-2. In particular, the present invention relates to a DNA segment encoding the coding sequence, or a unique portion thereof, for a third member of this receptor gene family, herein designated erbB-3.

BACKGROUND OF THE INVENTION

Proto-oncogenes encoding growth factor receptors constitute several distinct families with close overall structural homology. The highest degree of homology is observed in their catalytic domains, essential for the intrinsic tyrosine kinase activity of these proteins. Examples of such receptor families include: the EGF-R and the related product of the erbB-2 oncogene; the Colony Stimulating Factor 1 receptor (CSF-1-R) and the related Platelet-Derived Growth Factor receptor (PDGF-R); the insulin receptor (IF-R) and the related Insulin-like Growth factor 1 receptor (IGF-1-R); and the receptors encoded by the related oncogenes eph and elk.

It is well established that growth factor receptors in several of these families play critical roles in regulation of normal growth and development. Recent studies in Drosophila have emphasized how critical and multifunctional are developmental processes mediated by ligand-receptor interactions. An increasing number of Drosophila mutants with often varying phenotypes have now been identified as being due to lesions in genes encoding such proteins. The genetic locus of the Drosophila EGF-R homologue, designated DER, has recently been identified as being allelic to the zygotic embryonic lethal faint little ball exhibiting a complex phenotype with deterioration of multiple tissue components of ectodermal origin. Furthermore, other mutants appear to lack DER function either in the egg or the surrounding maternal tissue. Thus, the DER receptor may play an important role in the ligand-receptor interaction between egg and follicle cells necessary for determination of correct shape of eggshell and embryo. It is not yet known whether DER represents the sole the Drosophila counterpart of both known mammalian erbB-related genes.

Some of these receptor molecules have been implicated in the neoplastic process as well. In particular, both the erbB and erbB-2 genes have been shown to be activated as oncogenes by mechanisms involving overexpression or mutations that constitutively activate the catalytic activity of their encoded receptor proteins (Bargmann, C. I., Hung, M. C. & Weinberg, R. A., 1986, Cell 45:649-657; Di Fiore, P. P., Pierce, J. H., Kraus, M. H., Segatto, O., King, C. R. & Aaronson, S. A., 1987, Science 237:178-182; Di Fiore, P. P., Pierce, J. H., Fleming, T. P., Hazan, R., Ullrich, A., King, C. R., Schlessinger, J. & Aaronson, S. A., 1987, Cell 51:1063-1070; Velu, T. J., Beguinot, L., Vass, W. C., Willingham, M. C., Merlino, G. T., Pastan, I. & Lowy, D. R., 1987, Science 238:1408-1410). Both erbB and erbB-2 have been causally implicated in human malignancy. erbB gene amplification or overexpression, or a combination of both, has been demonstrated in squamous cell carcinomas and glioblastomas (Libermann, T. A., Nusbaum, H. R., Razon, N., Kris, R., Lax, I., Soreq, H., Whittle, N., Waterfield, M. D., Ullrich, A. & Schlessinger, J., 1985, Nature 313:144-147). erbB-2 amplification and overexpression have been observed in human breast and ovarian carcinomas (King, C. R., Kraus, M. H. & Aaronson, S. A., 1985, Science 229:974-976; Slamon, D. J., Godolphin, W., Jones, L. A., Holt, J. A., Wong, S. G., Keith, D. E., Levin, W. J., Stuart, S. G., Udove, J., Ullrich, A. & Press, M. F., 1989, Science 244:707-712), and erbB-2 overexpression has been reported to be an important prognostic indicator of particularly aggressive tumors (Slamon, D. J., et al., 1989, supra). Yet, not all such tumors have been found to overexpress erbB-2, and many human tumors have not yet been associated with any known oncogene. Thus, there has been a continuing need to search for additional oncogenes which would provide knowledge and methods for diagnosis and, ultimately, for rational molecular therapy of human cancers.

SUMMARY OF THE INVENTION

It is an object of present invention to provide a DNA segment encoding a receptor protein related to the erbB proto-oncogene family which previously has not been known or even suspected to exist. Further, it is an object of the present invention to develop assays for expression of the RNA and protein products of such genes to enable determining whether abnormal expression of such genes is involved in human cancers.

In pursuit of the above objects, the present inventors have discovered a human genomic DNA fragment that is produced by cleavage with the SacI restriction enzyme, has a size of about 9 kbp, and is detectable by nucleic acid hybridization with a probe derived from the v-erbB gene only under reduced stringency hybridization conditions. Thus, this DNA fragment is distinct from those known to encode the epidermal growth factor receptor (EGF-R) (i.e., the erbB gene) and from the related erbB-2 gene. Characterization of this DNA fragment after partial purification and molecular cloning showed that the region of v-erbB homology mapped to three exons that encode amino acid sequences having homologies of 64% and 67% to contiguous regions within the tyrosine kinase domains of the EGF-R and erbB-2 proteins, respectively. A probe derived from the genomic DNA clone identified cDNA clones of the related mRNA which encode a predicted 148 kd transmembrane polypeptide with structural features identifying it as a member of the erbB family, prompting designation of the new gene as erbB-3. This gene was mapped to human chromosome 12q11-13 and was shown to be expressed as a 6.2 kb transcript in a variety of normal tissues of epithelial origin. Markedly elevated erbB-3 mRNA levels were demonstrated in certain human mammary tumor cell lines.

Accordingly, in a principal embodiment, the present invention relates to a DNA segment having a nucleotide sequence that encodes an erbB-3 gene or a unique portion thereof. This portion of an erbB-3 gene includes at least about 12 to 14 nucleotides which are sufficient to allow formation of a stable duplex with a DNA or RNA segment having sequences complementary to those in this portion of an erbB-3 gene. Further, this unique portion of an erbB-3 gene, of course, has a sequence not present in an erbB or an erbB-2 gene. In other words, the sequence of this portion of an erbB-3 gene differs in at least one nucleotide from the sequence of any other DNA segment. In one embodiment, this DNA segment is exemplified by a human genomic DNA fragment that is produced by cleavage with the SacI restriction enzyme, has a size of about 9 kbp, and is detectable by nucleic acid hybridization with a probe derived from the v-erbB gen only under reduced stringency hybridization conditions, as described in Example 1. By application of the nucleic acid hybridization and cloning methods described in the present disclosure, without undue experimentation, one of ordinary skill in the art of recombinant DNA is enabled to identify and isolate DNA fragments related to the present human DNA fragment comprising a nucleotide sequence that encodes at least a portion of a mammalian erbB-3 gene other than the human erbB-3 gene. Application of the genomic DNA fragment of the erbB-3 gene as a probe in hybridization methods also enables one of ordinary skill in the art to obtain an entire erbB-3 gene, by sequential isolation of overlapping fragments adjoining the present fragment, i.e., by an approach known in the art as chromosome walking.

The present disclosure describes the partial nucleotide sequence of the human genomic 9 kbp SacI DNA fragment, within the region of homology to the v-erbB gene; however, the methods in the present disclosure further enable the isolation and determination of the sequence of the entire 9 kbp human genomic DNA fragment according to the present invention. Accordingly, the present invention further relates to a DNA segment having the nucleotide sequence, or a unique portion thereof, of a human genomic DNA fragment that is produced by cleavage with the SacI restriction enzyme, has a size of about 9 kbp, and is detectable by nucleic acid hybridization with a probe derived from the v-erbB gene only under reduced stringency hybridization conditions, as described in Example 1. By extension of the chromosome walking approach noted above, the present invention further enables one of ordinary skill in the art to determination of the sequences of related DNA fragments comprising the complete human erbB-3 gene as well as erbB-3 genes of, for example, mammals other than human.

In the application of the present SacI DNA fragment or any portion thereof as a probe for nucleic acid hybridization, the fragment is amplified, for example, by the in vitro polymerase chain reaction method (PCR; see U.S. Pat. No. 4,683,202; U.S. Pat. No. 4,683,195; and Saiki et al., 1985, Science 230:1350-54) or by standard methods of molecular cloning. For example, a clone of the human erbB-3 gene DNA segment according to the present invention is exemplified by a recombinant clone of a normal human thymus DNA fragment, herein designated as the E3-1 genomic clone, having the partial restriction enzyme map defined in FIG. 2 and the partial DNA sequence defined in FIG. 3 of the present application. Isolation and characterization of genomic clone E3-1 is described in Example 2, below.

Analysis of the nucleotide sequences of the human genomic DNA segment according to the present invention reveals that the nucleotide sequence encodes three open reading frames bordered by splice junction consensus sequences which define the boundaries between nontranslated intron sequences and the translated exons (FIG. 2). The predicted amino acid sequences of the three exons are highly similar to three regions which are contiguous in the tyrosine kinase domains of v-erbB, as well as human EGF-R and erbB-2 proteins. Moreover, the predicted amino acid sequences of this human genomic clone are included in a larger open reading frame in complementary DNA (cDNA) clones of an mRNA species that is detected by hybridization of a probe derived from the human genomic DNA clone.

Accordingly, the present invention also relates to a DNA segment having a nucleotide sequence of an erbB-3 gene in which that nucleotide sequence encodes the amino acid sequence of an erbB-3 gene or a unique portion thereof. In other words, the sequence of this portion of an erbB-3 amino acid sequence differs in at least one amino acid residue from the amino acid sequence encoded by any other DNA segment. This portion of an erbB-3 amino acid sequence includes at least about 4 to 6 amino acids which are sufficient to provide a binding site for an antibody specific for this portion of the erbB-3 polypeptide. Further, this unique portion of an erbB-3 amino acid sequence, of course, includes sequences not present in an erbB or an erbB-2 gene. In particular, the present invention relates to such a DNA segment for which this amino acid sequence or unique portion thereof is that of the polypeptide product of the human erbB-3 gene. This DNA segment is exemplified by the human genomic DNA clone E3-1, above, as well as by human cDNA clones designated E3-6, E3-8, E3-9, E3-11 and E3-16, which are described in Example 3 below. A preferred embodiment of this DNA segment that encodes the amino acid sequence of the entire polypeptide product of the human erbB-3 gene is human cDNA clone E3-16 having the nucleotide sequence defined in FIG. 4 (A-L) and having the predicted amino acid sequence defined in FIG. 4 (A-L).

The DNA segments according to this invention are useful for detection of expression of erbB-3 genes in normal and tumor tissues, as described in Example 5 below. Therefore, in yet another aspect, the present invention relates to a bioassay for detecting erbB-3 mRNA in a biological sample comprising the steps of: i) contacting that biological sample with a DNA segment of this invention under conditions such that a DNA:RNA hybrid molecule containing this DNA segment and complementary RNA can be formed; and ii) determining the amount of that DNA segment present in the resulting hybrid molecule. Findings described in Example 5, below, indicate that increased erbB-3 expression, as detected by this method of this invention, plays a role in some human malignancies, as is the case for the EGF-R (erbB) and erbB-2 genes.

Of course, it will be understood by one skilled in the art of genetic engineering that in relation to production of erbB-3 polypeptide products, the present invention also includes DNA segments having DNA sequences other than those in the present examples that also encode the amino acid sequence of the polypeptide product of an erbB-3 gene. For example, it is known that by reference to the universal genetic code, standard genetic engineering methods can be used to produce synthetic DNA segments having various sequences that encode any given amino acid sequence. Such synthetic DNA segments encoding at least a portion of the amino acid sequence of the polypeptide product of the human erbB-3 gene also fall within the scope of the present invention. Further, it is known that different individuals may have slightly different DNA sequences for any given human gene and, in some cases, such mutant or variant genes encode polypeptide products having amino acid sequences which differ among individuals without affecting the essential function of the polypeptide product. Still further, it is also known that many amino acid substitutions can be made in a polypeptide product by genetic engineering methods without affecting the essential function of that polypeptide. Accordingly, the present invention further relates to a DNA segment having a nucleotide sequence that encodes an amino acid sequence differing in at least one amino acid from the amino acid sequence of human erbB-3, or a unique portion thereof, and having greater overall similarity to the amino acid sequence of human erbB-3 than to that of any other polypeptide. The amino acid sequence of this DNA segment includes at least about 4 to 6 amino acids which are sufficient to provide a binding site for an antibody specific for the portion of a polypeptide containing this sequence. In a preferred embodiment, this DNA segment encodes an amino acid sequence having substantially the function of the human erbB-3 polypeptide. As noted above, the predicted erbB-3 polypeptide is a 148 kd transmembrane polypeptide with structural features identifying it as a member of the erbB receptor family.

The similarity of the amino acid sequence of the present invention with that of an erbB-3 amino acid sequence is determined by the method of analysis defined by the sequence alignment and comparison algorithms described by Pearson and Lipman (Pearson, W. R. & Lipman, D. J., 1988, Proc. Nat. Acad. Sci. U.S.A. 85:2444–48). This comparison contemplates not only precise homology of amino acid sequences, but also substitutions of one residue for another which are known to occur frequently in families of evolutionarily related proteins sharing a conserved function.

The present invention further relates to a recombinant DNA molecule comprising a DNA segment of this invention and a vector. In yet another aspect, the present invention relates to culture of cells transformed with a DNA segment according to this invention. These host cells transformed with DNAs of the invention include both higher eukaryotes, including animal, plant and insect cells, and lower eukaryotes, such as yeast cells, as well as prokaryotic hosts including bacterial cells such as those of E. coli and Eacillus subtilis. These aspects of the invention are exemplified by recombinant DNAs and cells described in Examples 2 and 3, below.

One particular embodiment of this aspect of this invention comprises a cell, preferably a mammalian cell, transformed with a DNA of the invention, wherein the transforming DNA is capable of being expressed to produce the functional polypeptide of an erbB-3 gene. For example, mammalian cells (COS-1) transformed with the pSV2 gpt vector carrying the E3-16 cDNA are prepared according to well-known methods, such as those described in U.S. Pat. Application 07/308,302 of Matsui et al., filed Feb. 9, 1989; see also Pierce, J. H. et al., 1988, Science 239:628–631; and Matsui, T., Heidaran, M., Miki, T., Popescu, N., La Rochelle, W., Kraus, M., Pierce, J. & Aaronson, S., 1989, Science 243:800–804). Briefly, cDNA expression plasmids are constructed by introducing the erbB-3-related cDNA encompassing all the nucleotides in the open reading frame into the pSV2 gpt vector into which the simian sarcoma virus long-terminal-repeat (LTR) had been engineered as the promoter, as previously described in detail. Transient expression an erbB-3 gene in such recombinant vectors is achieved by transection into COS-1 cells.

Stable expression of an erbB-3 gene can also be obtained with mammalian expression vectors such as the pZIPNEOSVX vector (Cepko, C. L., Roberts, B. E. and Mulligan, R. C., 1984, Cell 37:1053–62). For example, a eukaryotic expression vector was engineered by cloning the full-length erbB-3 coding sequence derived from cDNA clone E3-16 into the BamHI site of the pZIPNEOSVX vector DNA adapting the DNA fragments with synthetic oligonucleotides. NIH3T3 cells were transfected with 1 μg of recombinant expression vector DNA (LTRerbB-3) and selected with the resistance marker antibiotic G418. To detect expression of erbB-3, a polyclonal rabbit antiserum was raised against a synthetic peptide (amino acid positions 1191-1205) within the predicted carboxyl terminus of the erbB-3 coding sequence. As shown in FIG. 8, immunoblotting analysis led to detection of the erbB-3 protein (panel A). The specificity of erbB-3 protein detection was demonstrated by preincubating the antiserum with the homologous peptide (panel B). Moreover, the normal 180 kD erbB-3 protein was specifically detected with the polyclonal antiserum only in cell transfected with the recombinant erbB-3 expression vector, while control NIH3T3 cells that were not transfected with the vector were negative. The stably transfected NIH3T3 cells are useful as erbB-3 receptor protein sources for testing potential candidates for an erbB-3-specific ligand, analysis of the biological activity, as well as generation of monoclonal antibodies raised against the native erbB-3 protein. An erbB-3-specific ligand is identified by detection of autophosphorylation of the erbB-3 receptor protein, stimulation of DNA synthesis or induction of the transformed phenotype of the LTRerbB-3 transfected NIH3T3 cells.

Alternatively, other transformed cell systems are available for functional expression of receptors of the erbB receptor family, for example, a system based on the 32D cell line, a mouse hematopoietic cell line normally dependent on interleukin-3 (Il-3) for survival and proliferation. Recent studies have established that introduction of an expression vector for the EGF-R in these cells leads to effective coupling with EGF mitogenic signal transduction pathways, thereby allowing a ligand of the EGF-R to replace Il-3 in supporting survival and growth of the 32D cells. By employing the known methods described for the EGF-R, for example (Pierce, J. H. et al., 1988, supra), the E3-16 cDNA of the present invention is expressed to produce functional receptors in 32D cells which are then useful for examining the biological function of these erbB-3 receptors, for instance, the specificity of their ligand binding capacity and coupling capacities to secondary messenger systems. Thus, by so using gene expression methods described herein with the DNAs of the present invention, especially the preferred E3-16 cDNA clone, one of ordinary skill in the art, without undue experimentation, can construct cell systems which fall within the scope of this invention, for determining the mechanisms of erbB-3 regulatory processes. Accordingly, the present invention also relates to a bioassay for testing potential analogs of ligands of erbB-3 receptors for the ability to affect an activity mediated by erbB-3 receptors, comprising the steps of: i) contacting a molecule suspected of being a ligand with erbB-3 receptors produced by a cell producing functional erbB-3 receptors; and ii) determining the amount of a biological activity mediated by those erbB-3 receptors.

Various standard recombinant systems, such as those cited above as well as others known in the art, are suitable as well for production of large amounts of the novel erbB-3 receptor protein using methods of isolation for receptor proteins that are well known in the art. Therefore, the present invention also encompasses an isolated polypeptide having at least a portion of the amino acid sequence defined in FIG. 4.

This invention further comprises an antibody specific for a unique portion of the human erbB-3 polypeptide having the amino acid sequence defined in FIG. 4 (A-L), or a unique portion thereof. In this embodiment of the invention, the antibodies are monoclonal or polyclonal in origin, and are generated using erbB-3 receptor-related polypeptides or peptides from natural, recombinant or synthetic chemistry sources. These antibodies specifically bind to an erbB-3 protein which includes the sequence of such polypeptide. In other words, these antibodies bind only to erbB-3 receptor proteins and not to erbB (EGF-R) or erbB-2 proteins. Also, preferred antibodies of this invention bind to an erbB-3 protein when that protein is in its native (biologically active) conformation.

Fragments of antibodies of this invention, such as Fab or F(ab)' fragments, which retain antigen binding activity and can be prepared by methods well known in the art, also fall within the scope of the present invention. Further, this invention comprises a pharmaceutical composition of the antibodies of this invention, or an active fragment thereof, which can be prepared using materials and methods for preparing pharmaceutical compositions for administration of polypeptides that are well known in the art and can be adapted readily for administration of the present antibodies without undue experimentation.

These antibodies and active fragments thereof, can be used, for example, for specific detection or purification of the novel erbB-3 receptor. Such antibodies could also be used in various methods known in the art for targeting drugs to tissues with high levels of erbB-3 receptors, for example, in the treatment of appropriate tumors with conjugates of such antibodies and cell killing agents. Accordingly, the present invention further relates to a method for targeting a therapeutic drug to cells having high levels of erbB-3 receptors, comprising the steps of i) conjugating an antibody specific for an erbB-3 receptor, or an active fragment of that antibody, to the therapeutic drug; and ii) administering the resulting conjugate to an individual with cells having high levels of erbB-3 receptors in an effective amount and by an effective route such that the antibody is able to bind to the erbB-3 receptors on those cells.

The antibody of this invention is exemplified by rabbit antisera containing antibodies which specifically bind to erbB-3 protein. Such receptor specific antisera are raised to synthetic peptides representing a unique portion of the erbB-3 amino acid sequence, having six or more amino acids in sequences which are sufficient to provide a binding site for an antibody specific for this portion of the erbB-3 polypeptide. Further, this unique portion of an erbB-3 amino acid sequence, of course, includes sequences not present in an erbB or an erbB-2 amino acid sequence, as predicted by the respective cDNA sequences. The erbB-3 specific anti-peptide antibody of the present invention is exemplified by an anti-peptide antibody in polyclonal rabbit antiserum raised against the synthetic peptide having the sequence (in single letter amino acid code) EDEDEEYEYMNRRRR representing amino acid positions 1191-1205 in the predicted sequence of the erbB-3 polypeptide. The specific detection of erbB-3 polypeptide with this antiserum is illustrated in mammalian cells transformed with an expression vector carrying a human erbB-3 cDNA (see FIG. 8).

Antibodies to peptides are prepared by chemically synthesizing the peptides, conjugating them to a carrier protein, and injecting the conjugated peptides into rabbits with complete Freund's adjuvant, according to standard methods of peptide immunization. For example, the peptide is synthesized by standard methods (Merrifield, R. B., 1963, J. Amer. Soc., 85:2149) on a solid phase synthesizer. The crude peptide is purified by HPLC and conjugated to the carrier, keyhole limpet hemocyanin or bovine thyroglobulin, for example, by coupling the amino terminal cysteine to the carrier through a maleimido linkage according to well known methods (e.g., Lerner, R.A. et al., 1981, Proc. Nat. Acad. Sci. U.S.A., 78:3403). In one standard method of peptide immunology, rabbits are immunized with 100 μg of the erbB-3 peptide-carrier conjugate (1 mg/ml) in an equal volume of complete Freund's adjuvant and then boosted at 10-14 day intervals with 100 μg of conjugated peptide in incomplete Freund's adjuvant. Additional boosts with similar doses at 10-14 day intervals are continued until anti-peptide antibody titer, as determined, for example, by routine ELISA assays, reaches a plateau.

Thus, by following the teachings of the present disclosure, including application of generally known immunological methods cited herein, one of ordinary skill in the art is able to obtain erbB-3-specific antibodies and use them in a variety of immunological assays, for example, for diagnostic detection of unusually high or low expression in normal or tumor tissues. Thus, the present invention also relates to a bioassay for detecting an erbB-3 antigen in a biological sample comprising the steps of: i) contacting that sample with an antibody of the present invention specific for an erbB-3 polypeptide, under conditions such that a specific complex of that antibody and that antigen can be formed; and ii) determining the amount of that antibody present in the form of those complexes.

The present invention may be understood more readily by reference to the following detailed description of specific embodiments and the Examples and Figures included therein.

BRIEF DESCRIPTION OF THE DRAWINGS

FIG. 2. Genomic and cDNA cloning of erbB-3. The region of v-erbB homology within the genomic 9 kbp SacI insert of λE3-1 was subcloned into the plasmid pUC (pE3-1) and subjected to nucleotide sequence analysis. The three predicted exons are depicted as solid boxes. erbB-3 cDNA clones were isolated from oligo dT-primed libraries of mRNAs from normal human placenta (shaded bars) and the breast tumor cell line MCF-7 (open bar). The entire nucleotide sequence was determined for both strands on erbB-3 complementary DNA from normal human placenta and upstream of the 5' XhoI site on pE3-16. The coding sequence is shown as a solid bar and splice junctions of the three characterized genomic exons are indicated by vertical white lines. Solid lines in the cDNA map represent untranslated sequences. Restriction sites: A=AccI, Av-=AvaI, B=BamHI, Bg=BglII, E=EcoRI, H=HindIII, K=KpnI, M=MstII, P=PstI, S=SacI, Sm=SmaI, Sp=SpeI.

FIG. 3. Nucleotide sequence of the region of v-erbB homology in the human erbB-3 gene derived from human genomic DNA clone E3-1, in the 1.5 kbp region from the EcoRI to the PstI sites. This region contains three open reading frames bordered by splice junction consensus sequences (underlined). The predicted amino acid sequences of the three exons are shown in three letter code above the relevant DNA sequences.

FIG. 4 (A-L). Nucleotide sequence of the cDNA encoding the erbB-3 polypeptide and the predicted amino acid sequence of that polypeptide.

FIG. 5. Comparison of the predicted amino acid sequence of the erbB-3 polypeptide with other receptor-like tyrosine kinases. The amino acid sequence is shown in single letter code and is numbered on the left. The putative extracellular domain (light shading) extends between the predicted signal sequence (solid box) at the amino-terminus and a single hydrophobic transmembrane region (solid box) within the polypeptide. The two cysteine clusters (Cys) in the extracellular domain and the predicted tyrosine kinase domain (TK) within the cytoplasmic portion of the polypeptide are outlined by dark shading. The putative ATP-binding site at the amino-terminus of the TK domain is circled. Potential autophosphorylation sites within the carboxyl-terminal domain (COOH) are indicated by asterisks. Potential N-linked glycosylation sites(●-)are marked above the amino acid sequence. The percentage of amino acid homology of erbB-3 in individual domains with erbB-2, EGF-R, met, eph, insulin receptor (IR), and fms is listed below. Less than 16% identity is denoted by (-).

FIG. 8. Expression of a human erbB-3 polypeptide in cells transformed by a cDNA segment as detected by an erbB-3-specific anti-peptide antiserum. Cellular lysates (100 μg of each sample) were electrophoresed and transferred to nitrocellulose membranes for analysis by Western blotting. Panel A. Detection of erbB-3 polypeptide with the antiserum. Panel B. Preincubation of the antiserum with homologous peptide. Antibody blocking indicates binding specificity. Lane 1: Selected cultures of NIH3T3 cells transfected with 1 μg LTRerbB-3 expression vector. Lane 2: control NIH3T3 cells.

DESCRIPTION OF SPECIFIC EMBODIMENTS

Figure 1A:
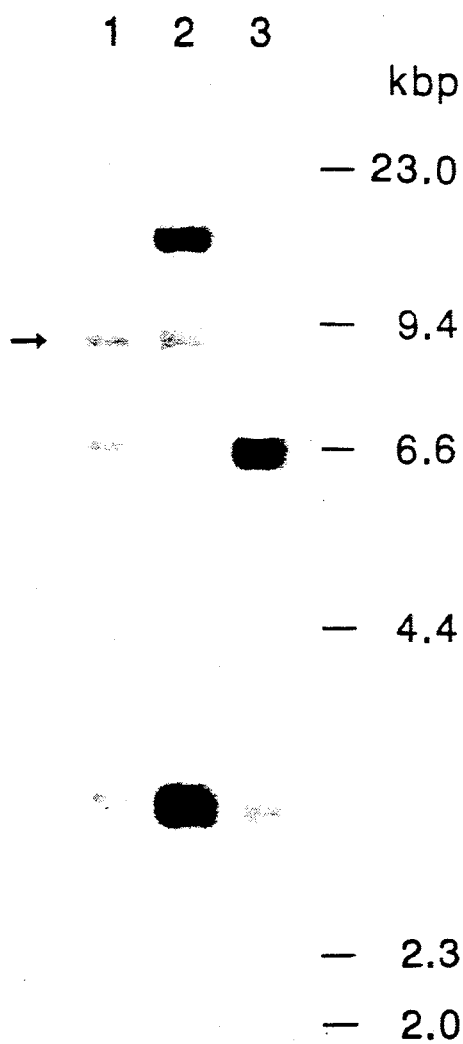
FIG. 1. Detection of v-erbB-related DNA fragments in DNAs from normal human thymus (lane 1), human mammary tumor lines MDA-MB468 (lane 2), and SK-BR-3 (lane 3). Hybridization was conducted at reduced (panel A) or intermediate (panel B) stringency conditions. The arrow denotes a novel 9 kilobase pair (kbp) erbB-related restriction fragment distinct from those of the EGF-R gene (erbB) and erbB-2.

The identification of a third member of the erbB-EGF receptor family of membrane spanning tyrosine kinases and the cloning of its full length coding sequence is described in the Examples herein. The presence of apparent structural domains resembling those of the EGF receptor suggests the existence of an extracellular binding site for a ligand. The structural relatedness of the extracellular domain of the erbB-3 receptor with that of the EGF receptor indicates that one or more of an increasing number of EGF-like ligands (Shoyab, M., Plowman, G. D., McDonald, V. L., Bradley, J. G. & Todaro, G. J., 1989, *Science* 243:1074-1076) interacts with the erbB-3 product. Accordingly, the erbB-3 gene is expected to play important roles in both normal and neoplastic processes, as is known for the EGF-R and erbB-2 genes.

Despite extensive collinear homology with the EGF receptor and erbB-2, distinct regions within the predicted erbB-3 coding sequence revealed relatively higher degrees of divergence. For example, its carboxyl terminal domain failed to exhibit significant collinear identity scores with either erbB-2 or EGF-R. The divergence at the carboxyl terminus also accounts for minor size differences among the three polypeptides of erbB-3, erbB-2, and EGF-R, which possess estimated molecular weights of 148 kilodaltons (kd), 138 kd, and 131 kd, respectively. Within the tyrosine kinase domain, which represents the most conserved region of the predicted erbB-3 protein, a short stretch of 29 amino acids closer to the carboxyl terminus than the ATP binding site differed from regions of the predicted erbB-2 and EGF-R coding sequence in 28 and 25 positions, respectively. Such regions of higher divergence in their cytoplasmic domains are likely to confer different functional specificity to these closely related receptor-like molecules. Thus, mutations or other alterations in expression of the erbB-3 gene are likely to cause cancers or genetic disorders different from those associated with such defects in the erbB and erbB-2 genes.

Chromosomal mapping localized erbB-3 to human chromosome 12 at the q11-13 locus, whereas the related EGF-R and erbB-2 genes are located at chromosomal sites 7p12-13 and 17p12-21.3, respectively. Thus, each gene appears to be localized to a region containing a different homeobox and a different collagen chain gene locus. Keratin type I and type II genes also map to regions of 12 and 17, respectively, consistent with the different localizations of erbB-3 and erbB-2, respectively. Thus, the DNA segments of the present invention represent novel probes to aid in genetic mapping of any heritable diseases which are associated with chromosomal aberrations in the vicinity of the 12q11-13 locus.

There is evidence for autocrine as well as paracrine effectors of normal cell proliferation. The former are factors that are produced by the same cells upon which they stimulate cell proliferation, whereas the latter factors are secreted by cells other than those that are affected by those factors. However, the inherent transforming potential of autocrine growth factors suggests that growth factors most commonly act on their target cell populations by a paracrine route. The present survey of erbB-3 gene expression indicates its normal expression in cells of epithelial and neuroectodermal derivation. Comparative analysis of the three erbB receptor-like genes in different cell types of epidermal tissue revealed that keratinocytes expressed all three genes. In contrast, melanocytes and stromal fibroblasts specifically lacked EGF-R and erbB-3 transcripts, respectively. Thus, melanocytes and stromal fibroblasts may be sources of paracrine growth factors for EGF-R and erbB-3 products, respectively, that are expressed by the other cell types residing in close proximity in epidermal tissues.

Given that both erbB and erbB-2 have been causally implicated in human malignancy, the present findings (Example 5) that the erbB-3 transcript is overexpressed in a significant fraction of human mammary tumor cell lines indicates that this new member of the EGF-R receptor family also plays an important role in some human malignancies.

EXAMPLE 1

Identification of a human DNA fragment related to the erbB proto-oncogene family.

In an effort to detect novel erbB-related genes, human genomic DNA was cleaved with a variety of restriction endonucleases and subjected to Southern blot analysis with v-erbB as a probe. Normal mammary epithelial cells AB589 (Walen, K. H. & Stampfer, M. R., 1989, *Cancer. Genet. Cytogenet.* 37:249-261) and immortalized keratinocytes RHEK have been described previously (Rhim, J. S., Jay, G., Arnstein, P., Price, F. M., Sanford, K. K. & Aaronson, S. A., 1985, *Science* 227:1250-52). Normal human epidermal melanocytes (NHEM) and keratinocytes (NHEK) were obtained from Clonetics. Sources for human embryo fibroblasts (Rubin, J. S., Osada, H., Finch, P. W., Taylor, W. G., Rudikoff, S., & Aaronson, S. A., 1989, *Proc. Nat. Acad. Sci. U.S.A.* 86:802-806) or mammary tumor cell lines SK-BR-3, MDA-MB468, MDA-MB453, and MDA-MB415 (Kraus, M. H., Popescu, N. C., Amsbaugh, S. C. & King, C. R., 1987, *EMBO. J.* 6:605-610) have been described. For nucleic acid RNA hybridization, DNA and RNA were transferred to nitrocellulose membranes as previously described (Kraus, M. H., et al., 1987, supra). High stringency hybridization was conducted in 50% formamide and 5xSSC at 42° C. Filters were washed at 50° C. in 0.1xSSC. Reduced stringency hybridization of DNA was carried out in 30% formamide followed by washes in 0.6xSSC, while intermediate stringency was achieved by hybridization in 40% formamide and washing in 0.25xSSC. For the specific results depicted in FIG. 1, DNAs were restricted with SacI and hybridized with probe specific for an oncogenic viral form of the erbB gene, v-erbB, spanning from the upstream BamHI site to the EcoRI site in the avian erythroblastosis proviral DNA (Vennstrom, B., Fanshier, L., Moscovici, C. & Bishop, J. M., 1980, *J. Virol.* 36:575-585).

Figure 1B:
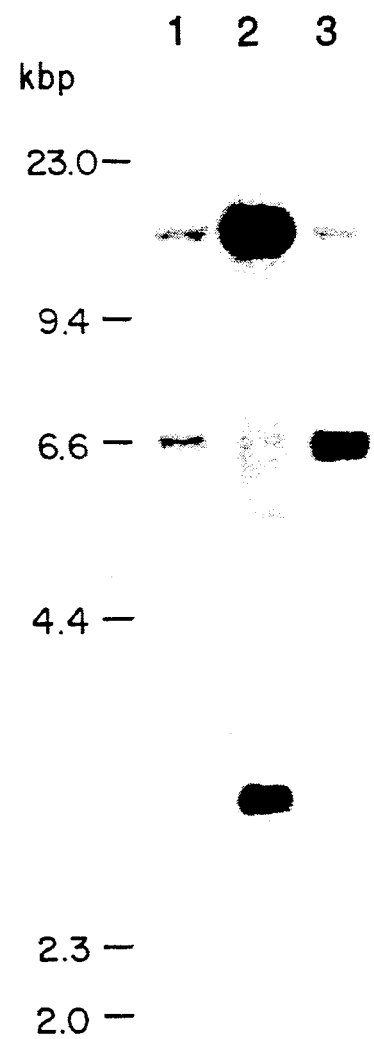

Under reduced stringency hybridization, four SacI restriction fragments were detected. Two were identified as EGF-R gene fragments by their amplification in the mammary tumor cell line MDA-MB468 (FIG. 1A, lane 1,2) known to contain EGF-R gene amplification and one as an erbB-2 specific gene fragment due to its increased signal intensity in another mammary tumor cell line, SK-BR-3, known to have erbB-2 amplified (FIG. 1A, lane 1,3). However, a single 9 kbp SacI fragment exhibited equal signal intensities in DNAs from normal human thymus, SK-BR-3 and a line with high levels of EGF-R, A431 (FIG. 1A). When the hybridization stringency was raised by 7° C., this fragment did not hybridize, whereas EGF-R and erbB-2 specific restriction fragments were still detected with v-erbB as a probe (FIG. 1B). Taken together, these findings suggested the specific detection of a novel v-erbB-related DNA sequence within the 9 kbp SacI fragment.

EXAMPLE 2

Cloning of the human DNA fragment related to erbB.

For further characterization a normal human genomic library was prepared from SacI cleaved thymus DNA enriched for 8 to 12 kbp fragments. For convenience, bacteriophage λsep6-lac5 was obtained from L. Prestidge and D. Hogness (Stanford University); many other cloning vectors derived from phage λ or other genomes can be used for cloning this DNA fragment according to standard recombinant DNA methods that are well known in the art. Purified phage DNA was subjected to cos-end ligation, restriction with SacI, and fractionation in a continuous 10-40% sucrose gradient. A genomic library was prepared by ligating SacI restriction fragments of normal human thymus DNA in the molecular weight range of 8 kbp to 12 kbp (isolated by sucrose gradient sedimentation) with the purified phage arms. Ten recombinant clones detected by v-erbB under reduced stringency conditions did not hybridize with human EGF-R or erbB-2 cDNA probes at high stringency. As shown in the restriction map of a representative clone with a 9 kbp insert, the region of v-erbB homology was localized by hybridization analysis to a 1.5 kbp segment spanning from the EcoRI to the downstream PstI site.

The nucleotide sequence of a portion of a clone of the novel human genomic DNA fragment related to erbB was determined for both DNA strands by the dideoxy chain termination method (Sanger, F., Nicklen, S. & Coulson, A. R., 1977, *Proc. Nat. Acad. Sci. U.S.A.* 74:5463-67) using supercoiled plasmid DNA as template. The nucleotide sequence was assembled and translated using IntelliGenetics software. Amino acid sequence comparison was performed with the alignment program by Pearson and Lipman (Pearson, W. R. & Lipman, D. J., 1988, supra) as implemented on the computers of the NCI Advanced Scientific Computing Laboratory. Hydrophobic and hydrophilic regions in the predicted protein were identified according to Kyte and Doolittle (Kyte, J. & Doolittle, R. F., 1982, *J. Mol. Biol.* 157:105-132). Nucleotide sequence analysis revealed that the region of v-erbB homology in the 1.5 kbp segment from the EcoRI to the PstI contained three open reading frames bordered by splice junction consensus sequences (FIG. 2). Computerized comparisons of the predicted amino acid sequence of these three open reading frames with other known proteins revealed the highest identity scores of 64% to 67% to three regions which are contiguous in the tyrosine kinase domains of v-erbB, as well as human EGF-R and erbB-2 proteins. Furthermore, all splice junctions of the three characterized exons in the new gene were conserved with erbB-2. Amino acid sequence homology to other known tyrosine kinases was significantly lower, ranging from 39% to 46%.

A single 6.2 kb specific mRNA was identified by Northern blot analysis of human epithelial cells using the 150 bp SpeI-AccI exon-containing fragment as probe (FIG. 2). Under the stringent hybridization conditions employed, this probe detected neither the 5 kb erbB-2 mRNA nor the 6 kb and 10 kb EGF-R mRNAs. All of these findings suggested that the present work has identified a new functional member of the erbB proto-oncogene family, which tentatively has been designated as erbB-3.

EXAMPLE 3

Cloning and characterization of cDNAs for the mRNA of the human erbB-3 gene.

In an effort to characterize the entire erbB-3 coding sequence, overlapping cDNA clones were isolated from oligo dT-primed cDNA libraries from sources with known erbB-3 expression, utilizing gene-specific genomic exons or cDNA fragments as probes. In brief, an oligo dT-primed human placenta cDNA library in λgt11 was obtained from Clontech. MCF-7 cDNA was prepared by first strand synthesis from 5 μg poly A+ RNA using an oligo dT containing linker-primer and Mo-MuLV reverse transcriptase, followed by second strand synthesis with DNA polymerase I, RNaseH, and subsequent T4 DNA polymerase treatment. Double-stranded cDNA was directionally cloned into the SfiI site of λpCEV9 using specific linker-adapter oligonucleotides (Miki, T., Matsui, T., Heidaran, M. A. & Aaronson, S. A., 1989, Gene 83:137–146; see also, U.S. Application Ser. No. 07/386,053 of Miki et al., filed Jul. 28, 1989). Following plaque purification, phage DNA inserts were subcloned into pUC-based plasmid vectors for further characterization. The clones were initially characterized by restriction analysis and hybridization to the mRNA, and were subsequently subjected to nucleotide sequence analysis. Clones designated pE3-6, pE3-8, pE3-9, and pE3-11 carrying inserts with molecular weights ranging from 1.3 kbp to 4.3 kbp were isolated from a human placenta library, whereas the pE3-16 clone containing a 5 kbp insert was obtained by screening the MCF-7 cDNA library with the upstream most coding sequence of pE3-11 as a probe. The clones pE3-8, pE3-9, pE3-11, and pE3-16 contained identical 3' ends terminating in a poly A stretch (FIG. 2).

The complete coding sequence of erbB-3 was contained within a single long open reading frame of 4080 nucleotides extending from position 46 to an in-frame termination codon at position 4126. The most upstream ATG codon at position 100 was the likely initiation codon, as it was preceded by an in-frame stop codon at nucleotide position 43 and fulfilled the criteria of Kozak for an authentic initiation codon. The open reading frame comprised 1342 codons predicting a 148 kd polypeptide. Downstream from the termination codon, multiple stop codons were present in all frames. As shown in FIG. 5, the deduced amino acid sequence of the erbB-3 polypeptide predicted a transmembrane receptor tyrosine kinase most closely related to EGF-R and erbB-2. A hydrophobic signal sequence of erbB-3 was predicted to comprise the 19 amino-terminal amino acid residues. Cleavage of this signal sequence between glycine at position 19 and serine at position 20 would generate a processed polypeptide of 1323 amino acids with an estimated molecular weight of 145 kd. A single hydrophobic membrane spanning domain encompassing 21 amino acids was identified within the coding sequence separating an extracellular domain of 624 amino acids from a cytoplasmic domain comprising 678 amino acids (FIG. 5).

The putative erbB-3 ligand-binding domain was 43% and 45% identical in amino acid residues with the predicted erbB-2 and EGF-R protein, respectively. Within the extracellular domain, all 50 cysteine residues of the processed erbB-3 polypeptide were conserved and similarly spaced when compared to the EGF-R and erbB-2. Forty-seven cysteine residues were organized in two clusters containing 22 and 25 cysteines respectively, a structural hallmark of this tyrosine kinase receptor subfamily (see, for example, Yamamoto, T., Ikawa, S., Akiyama, T., Semba, K., Nomura, N., Miyajima, N., Saito, T. & Toyoshima, K., 1986, Nature 319:230–234). Ten potential N-linked glycosylation sites were localized within the erbB-3 extracellular domain. In comparison with the EGF-R and erbB-2 proteins, five and two of these glycosylation sites were conserved, respectively. Among these, the site proximal to the transmembrane domain was conserved among all three proteins (FIG. 5).

Within the cytoplasmic domain, a core of 277 amino acids from position 702 through 978 revealed the most extensive homology with the tyrosine kinase domains of EGF-R and erbB-2. In this region 60% or 62% of amino acid residues were identical and 90% or 89% were conserved, respectively. This stretch of amino acid homology coincides with the minimal catalytic domain of tyrosine kinases (Hanks, S. K., Quinn, A. M. & Hunter, T., 1988, Science 241:42–52). There was significantly lower homology with other tyrosine kinases (FIG. 5). The consensus sequence for an ATP-binding site GxGxxG (Hanks, S. K. et al., 1988, supra) was identified at amino acid positions 716 through 721. This sequence as well as a lysine residue located 21 amino acid residues further toward the carboxyl terminus were conserved between the three erbB-related receptors. Taken together these findings defined the region between amino acid position 702 and 978 as the putative catalytic domain of the erbB-3 protein (FIG. 5).

The most divergent region of erbB-3 compared to either EGF-R or erbB-2 was its carboxyl terminus comprising 364 amino acids. This region showed a high degree of hydrophilicity and the frequent occurrence of proline and tyrosine residues. Among these tyrosine residues, those at positions 1197, 1199, and 1262 matched closest with the consensus sequence for putative phosphorylation sites. The peptide sequence YEYMN, encompassing tyrosine 1197 and 1199, was repeated at positions 1260–1264 and was at both locations surrounded by charged residues, providing an environment of high local hydrophilicity. These observations render tyrosines 1197, 1199 and 1262 likely candidates for autophosphorylation sites of the erbB-3 protein.

EXAMPLE 4

Chromosomal mapping of the human erbB-3 gene.

Figure 6:
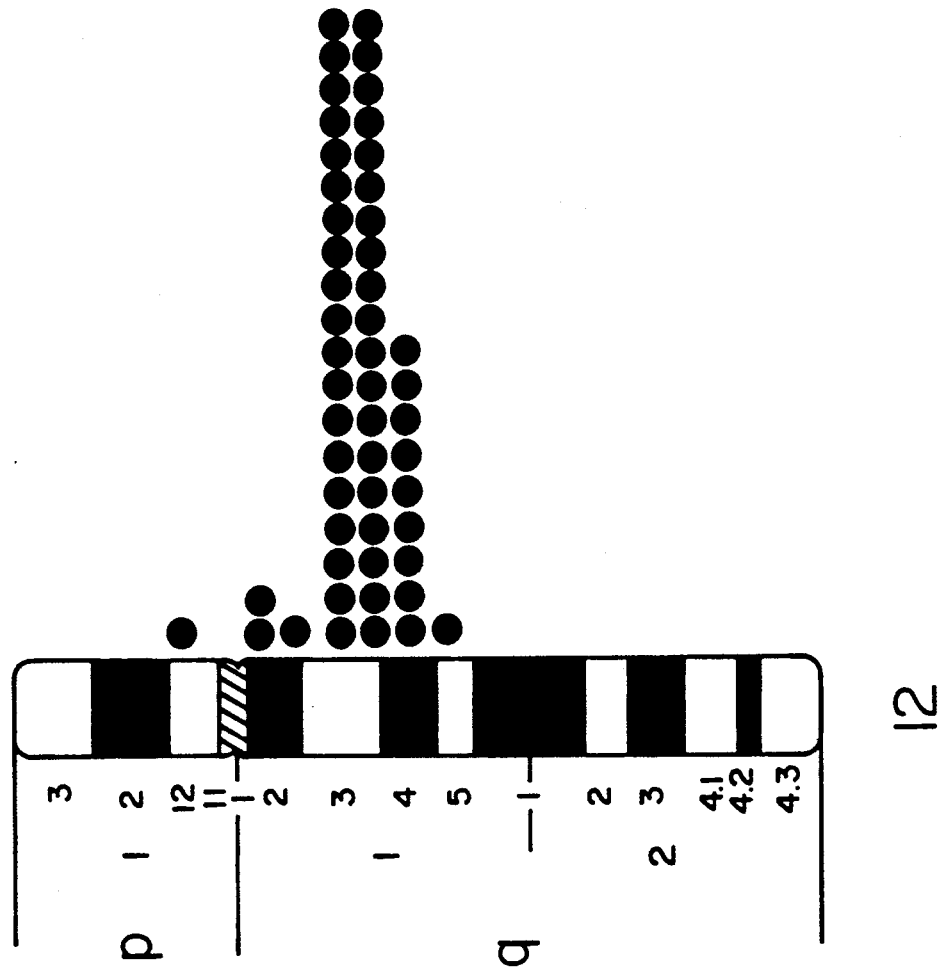
FIG. 6. Assignment of the genomic locus of erbB-3 was assigned to human chromosomal locus 12q13. A total of 142 grains were localized on the 400-band ideogram. As depicted in the diagram, specific labeling of chromosome 12 was observed, where 38 out of 51 grains were localized to band q13.

The chromosomal location of the erbB-3 gene was determined by in situ hybridization (Popescu, N. C., King, C. R. & Kraus, M. H., 1989, Genomics 4:362–366) with a $^3$H-label ed plasmid containing the amino-terminal erbB-3 coding sequence. A total of 110 human chromosome spreads were examined prior and subsequent to G banding for identification of individual chromosomes. A total of 142 grains were localized on a 400-band ideogram. Specific labeling of chromosome 12 was observed, where 38 out of 51 grains were localized to band q13 (FIG. 6). Thus, the genomic locus of erbB-3 was assigned to 12q13. In this region of chromosome 12, several genes have previously been mapped including the melanoma-associated antigen ME491, histone genes and the gene for lactalbumin. In addition, two proto-oncogenes, int-1 and gli are located in close proximity to erbB-3.

EXAMPLE 5

ErbB-3 expression in normal and malignant human cells.

To investigate its pattern of expression, a number of human tissues were surveyed for the erbB-3 transcript. The 6.2 kb erbB-3 specific mRNA was observed in term placenta, postnatal skin, stomach, lung, kidney, and brain, while it was not detectable in skin fibroblasts, skeletal muscle or lymphoid cells. Among the fetal tissues analyzed, the erbB-3 transcript was expressed in liver, kidney, and brain, but not in fetal heart or embryonic lung fibroblasts. These observations indicate the preferential expression of erbB-3 in epithelial tissues and brain.

ErbB-3 expression was also investigated in individual cell populations derived from normal human epithelial tissues including keratinocytes, glandular epithelial cells, melanocytes, and fibroblasts. For comparison levels of EGF-R and erbB-2 transcripts were analyzed. As shown in Table 1, erbB-3 mRNA levels were relatively high in keratinocytes, comparable with those of erbB-2 and EGF-R in these cells. Lower, but similar expression levels of each transcript were detected in cells

TABLE 1

Normal expression pattern of human erbB gene family members.

| Cell Source of Transcripts | Gene | Relative RNA levels |
|---|---|---|
| Embryonic fibroblast (M426) | erbB-3 | — |
| | erbB-2 | + |
| | EGF-R | + |
| Skin fibroblast (501T) | erbB-3 | — |
| | erbB-2 | + |
| | EGF-R | + |
| Immortal keratinocyte (RHEK) | erbB-3 | ++ |
| | erbB-2 | ++ |
| | EGF-R | ++ |
| Primary keratinocyte (NHEK) | erbB-3 | + |
| | erbB-2 | + |
| | EGF-R | ++ |
| Glandular epithelium (AB589) | erbB-3 | (+) |
| | erbB-2 | (+) |
| | EGF-R | (+) |
| Melanocyte (NHEM) | erbB-3 | ++ |
| | erbB-2 | ++ |
| | EGF-R | — |

Replicate Northern blots were hybridized with equal amounts (in cpm) of probes of similar specific activities for erbB-3, erbB-2, and EGF-R, respectively. Relative signal intensities were estimated: − not detectable. (+) weakly positive, + positive. ++ strongly positive.

derived from glandular epithelium. These findings are consistent with growth regulatory roles of all three receptor-like molecules in squamous and glandular epithelium. Whereas erbB-2 and EGF-R transcripts were also readily observed in normal fibroblasts, the same cells lacked detectable erbB-3 mRNA. In contrast, normal human melanocytes, which expressed both erbB-3 and erbB-2 at levels comparable with human keratinocytes, lacked detectable EGF-R transcripts. Thus, the expression patterns of these receptor-like molecules were different in specialized cell populations derived from epidermal tissues.

Figure 7A:
FIG. 7. Elevated erbB-3 transcript levels in human mammary tumor cell lines. A Northern blot containing 10 μg total cellular RNA from AB589 mammary epithelial cells (lane 1), as well as mammary tumor cell lines MDA-MB415 (lane 2) and MDA-MB453 (lane 3) was hybridized with an erbB-3 cDNA probe (panel A). Following signal decay the same blot was rehybridized with a human β-actin cDNA probe (Gunning, P., Ponte, P., Okayama, H., Engel, J., Blau, H. & Kedes, L., 1983, *Mol. Cell Biol.* 3:787-795) (panel B).
Figure 7B:

To search for evidence of erbB-3 involvement in the neoplastic process, erbB-3 mRNA levels in a series of human tumor cell lines were surveyed. The erbB-3 transcript was detected in 36 of 38 carcinomas and 2 of 12 sarcomas while 7 tumor cell lines of hematopoetic origin lacked measureable erbB-3 mRNA. Markedly elevated levels of a normal-sized transcript were observed in 6 out of 17 tumor cell lines derived from human mammary carcinomas. By Southern blot analysis, neither gross gene rearrangement nor amplification was detected in the cell lines. FIG. 7A shows the results of Northern blot analysis with control AB589 non-malignant human mammary epithelial cells (lane 1) and two representative human mammary tumor lines, MDA-MB415 (lane 2) and MDA-MB453 (lane 3). Hybridization of the same filter with a human $\beta$-actin probe (FIG. 7B) verified actual levels of mRNA in each lane. Densitometric scanning indicated that the erbB-3 transcript in each tumor cell line was elevated more than 100 fold above that of the control cell line. Thus, overexpression of this new member of the erbB family, as in the case of the EGF-R and erbB-2 genes, is likely to play an important role in some human malignancies.

For purposes of completing the background description and present disclosure, each of the published articles, patents and patent applications heretofore identified in this specification are hereby incorporated by reference into the specification.

The foregoing invention has been described in some detail for purposes of clarity and understanding. It will also be obvious that various changes and combinations in form and detail can be made without departing from the scope of the invention.

What is claimed is:

1. A DNA isolate consisting essentially of the nucleotide sequence of an erbB-3 gene defined in FIG. 4.

2. The DNA isolate according to claim 1 consisting of human cDNA clone E3-16.

3. A DNA isolate consisting essentially of the nucleotide sequence of a genomic DNA fragment capable of being produced by cleavage with the SacI restriction enzyme, having a size of about 9kb and being detectable by nucleic acid hybridization with a probe derived from the v-erbB gene under reduced hybridization stringency conditions, wherein said isolate is the human genomic DNA clone E3-1 having the partial restriction enzyme map defined in FIG. 2 and the partial DNA sequence defined in FIG. 3.

4. A DNA isolate consisting essentially of a portion of the nucleotide sequence as defined in FIG. 4 that encodes a portion of erbB-3 protein sufficient to provide an erbB-3 receptor protein binding site for an antibody thereto which is further characterized by not binding to erbB-2 or erbB receptor protein.

5. The DNA isolate according to claim 4 having the function of a DNA probe for specific recognition of the erbB-3 gene and further characterized by not hybridizing to erbB-2 or erbB.

6. The DNA isolate according to claim 4 that encodes an amino acid sequence having the ligand binding function of the human erbB-3 polypeptide.

7. A vector comprising the DNA isolate according to claim 4.

8. A culture of cells transformed in vitro with the DNA isolate according to claim 4.

* * * * *